United States Patent [19]

Sarneel

[11] Patent Number: Plant 5,394

[45] Date of Patent: Jan. 22, 1985

[54] CARNATION NAMED ODEON

[75] Inventor: J. F. Sarneel, Nieuwveen, Netherlands

[73] Assignee: M. Lek en Zonen, B.V. Nieuwveen, Netherlands

[21] Appl. No.: 508,864

[22] Filed: Jun. 29, 1983

[51] Int. Cl.[3] ..... A01H 5/00

[52] U.S. Cl. ..... Plt./70

[58] Field of Search ..... Plt./70

*Primary Examiner*—Robert E. Bagwill

*Attorney, Agent, or Firm*—Chas W. Rummler; John B. Lingmus

[57] ABSTRACT

A new variety of carnation plant distinguished by a continuous and profuse production of medium sized flowers having a generally orange coloration borne on long, strong flower stems growing raceme on strong main stems of about one meter in length, the plant being of the spray type with a vigorous and rapid growth rate with strong stem character and with abundant foliage.

1 Drawing Figure

BACKGROUND OF THE NEW PLANT

This new carnation variety originated as a seedling of unknown parentage growing among a field of hybrids produced by cross-pollinization of selected plants of unrecorded origin maintained in nursery facilities for breeding purposes at Nieuwveen, Netherlands, the object being to develop plants having improved flower production and growing quality. This plant was selected by me because of its high production of generally orange colored blossoms and was promptly reproduced by means of cuttings to test its growth and flower production characteristics. I propagated this plant through successive generations at Nieuwveen, Netherlands, and found that its distinctive characteristics held true from generation to generation and appeared to be firmly fixed. Because of the unique coloration of its relatively long stemmed blooms, its vigorous and continued production of flowers and its vigorous growth habit, this plant is now being commercially propagated both at Nieuwveen, Netherlands, and at Wheat Ridge, Colo., U.S.A.

DESCRIPTION OF THE DRAWINGS

My new carnation variety is illustrated by the accompanying full color photographic drawings which show, in the left hand view, a number of stems bearing buds at various stages of opening and several fully opened flowers, and in the right hand view, face views of two of the flowers; the colors shown being as nearly true as it is reasonably possible to reproduce by conventional commercial photographic procedures.

DESCRIPTION OF THE NEW PLANT

The following is a detailed description of my new carnation plant based upon observations of greenhouse grown plants made at Wheat Ridge, Colo., in March and April of 1983, the color designations being according to The R.H.S. Colour Chart of The Royal Horticultural Society of London, England.

THE PLANT

Origin: Seedling.

Parentage: Unknown. This seedling was produced by cross-pollinization of selected plants of unknown parentage maintained for breeding purposes.

Classification:

*Botanic.*—*Dianthus caryophyllus.*

*Commercial.*—Greenhouse carnation for cut flower production.

Form: bush, with tall spray-type shape.

Height: About one meter.

Growth rate: Very rapid.

Growth habit: Vigorous with strong stem character.

Branching character: Alternate.

Foliage:

*Quantity.*—Abundant.

*Character of leaf.*—About 45 mm. in length, sessile and with irregularly crenated margins.

*Texture.*—Leathery.

*Color.*—Upper side — Blue Green. Under side — Blue Green.

*Leaflets.*—None.

THE BUD

Size: Medium.

*Diameter.*—About 15 mm.

*Length.*—About 30 mm.

Shape: Inverted pear shaped.

Rate of opening: With a mature bud, the flower will appear about five days after sepals begin to open.

Color of petals:

*When sepals first divide.*—Light Orange.

*When petals begin to unfurl.*—Light Orange.

Sepals: Hooded over the bud at the beginning and standing up when the flowers open.

Calyx:

*Shape.*—Cylindrical to funnel shape with returned calyx teeth.

*Size.*—Medium to long and pointed.

*Splitting.*—Calyx does not split.

*Aspect.*—Smooth.

Character of flower stem: Rigid and erect.

*Color.*—Green.

THE FLOWER

Blooming habit: Continuous and profusely.

Size of bloom: Medium.

*Diameter.*—About 60 mm.

*Depth.*—About 25 mm.

Borne: Raceme with at least three blooms on each main stem.

Shape:

*When bloom first opens.*—Generally flat.

*When bloom matures.*—Flattened convex.

Petalage:

*Number of petals.*—Forty-six.

*Arrangement.*—Imbricated.

*Form.*—Fan shaped and transversely undulated with longitudinally extending waves.

*Margin type.*—Dentated.

*Texture.*—Soft.

*Appearance.*—Velvety.

*Color.*—Outer petals: Body — Close to R.H.S. 28D with a color close to R.H.S. 29A at the base, occasionally striped with red, mostly wedge shaped, stripes to about 10 mm. long and 2 mm. wide.

*Claw.*—Length — About 29 mm.

REPRODUCTIVE ORGANS

Stamens:

*Number.*—Four.

*Arrangement.*—Regular.

*Anthers.*—Size: About 4 mm. Color: Straw Yellow.

*Filaments.*—Length — About 30 mm. Color — Almost White.

*Pollen.*—Color — Yellow.

Pistils:

*Number.*—Two.

*Styles.*—Length — 20 to 40 mm. Color — Pinkish White.

*Stigmas.*—Color — White.

Characteristics of ovaries: Spindle shaped with Green top and Whitish bottom

I claim:

1. A new and distinct carnation cultivar, substantially as herein shown and described, charcterized by its year round production of generally orange colored, medium sized blossoms, and by its continuous profuse production of blooms substantially the year round.

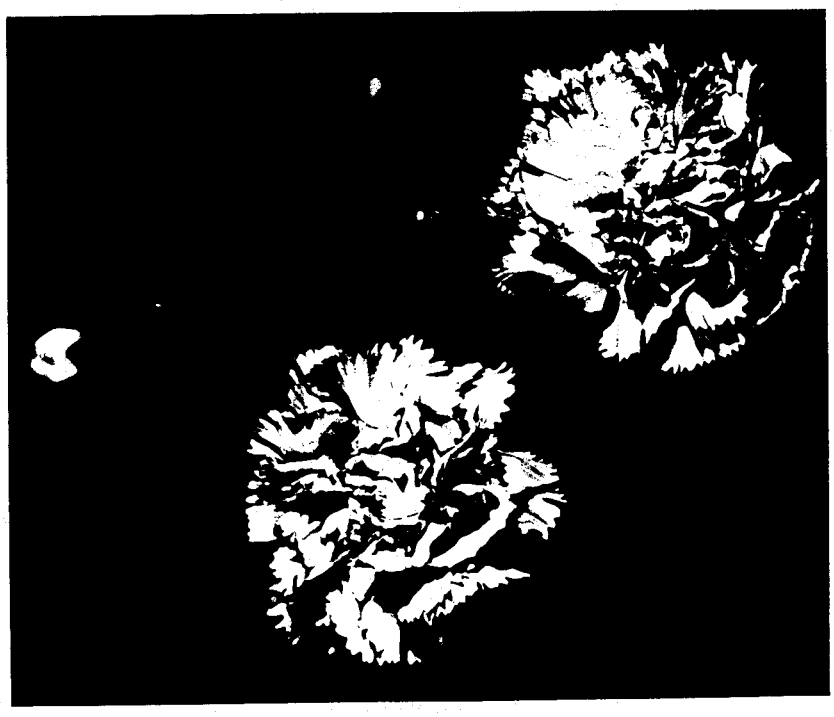
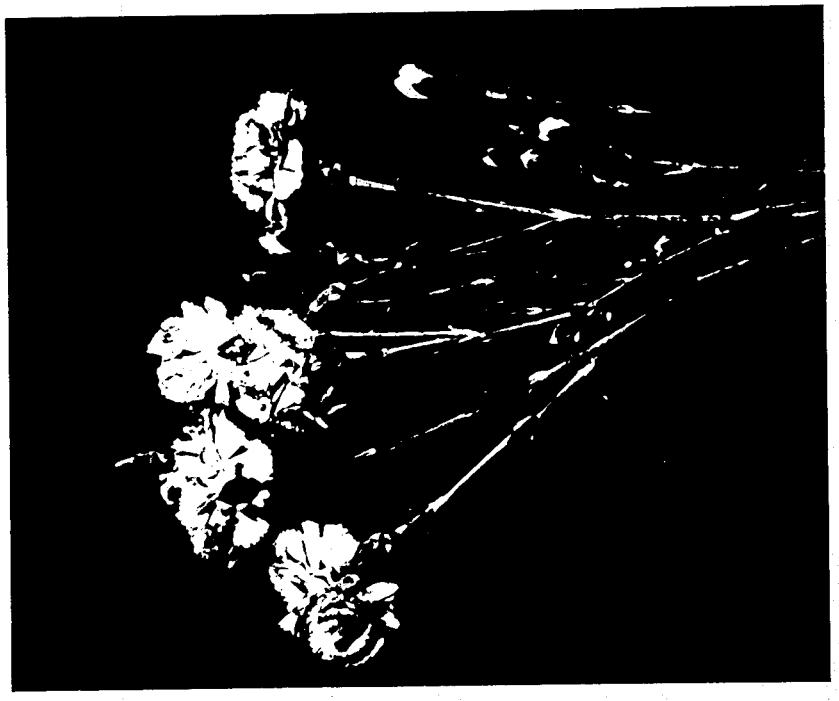

* * * * *